US006204283B1

(12) United States Patent
Black et al.

(10) Patent No.: US 6,204,283 B1
(45) Date of Patent: Mar. 20, 2001

(54) PARASITIC MITE CONTROL ON BENEFICIAL INSECTS

(75) Inventors: Bruce Christian Black, Yardley, PA (US); William R. Baumbach, Hopewell; Michael P. Beluch, Belle Mead, both of NJ (US)

(73) Assignee: American Cyanamid Company

( * ) Notice: Subject to any disclaimer, the term of this patent is extended or adjusted under 35 U.S.C. 154(b) by 0 days.

(21) Appl. No.: 09/351,222

(22) Filed: Jul. 12, 1999

Related U.S. Application Data

(60) Provisional application No. 60/092,773, filed on Jul. 14, 1998.
(51) Int. Cl.[7] ........................ A61K 31/415; C07D 231/10
(52) U.S. Cl. ........................................ 514/406; 548/374.1
(58) Field of Search ........................... 548/379.4, 374.1; 514/359, 406

(56) References Cited

U.S. PATENT DOCUMENTS 4,950,668    8/1990   Okada et al. ..................... 514/232.2

OTHER PUBLICATIONS

Okada, Itaru et. al., Discovery of Novel Acaricide Pyranica, Res. Dev. Rev., vol. 8(1), pp. 50–58, 1994.*

* cited by examiner

*Primary Examiner*—Zinna Northington Davis
*Assistant Examiner*—Binta Robinson
(74) *Attorney, Agent, or Firm*—John W. Hogan; Barbara V. Maurer

(57) ABSTRACT

The present invention provides a method to control parasitic mites on beneficial insects, such as honeybees, via the application of a parasiticidally effective amount of tebufenpyrad.

17 Claims, No Drawings

PARASITIC MITE CONTROL ON BENEFICIAL INSECTS

This application claims priority from copending provisional application Ser. No. 60/092,773 filed on Jul. 14, 1998.

BACKGROUND OF THE INVENTION

Beneficial insects, particularly the honeybee are susceptible to infestation and damage caused by parasitic mites. Recently, a plague of parasitic mites has significantly decreased the honeybee population. Honeybees are important for crop pollination and aid in fruit formation and size and enhance crop yield. Known measures of control of the parasitic mite populations are few and unpredictable.

Tebufenpyrad and the insecticidal and acaricidal use thereof is described in U.S. Pat. No. 4,950,668. However, the selective application of tebufenpyrad to beneficial insects is undisclosed.

Therefore, new methods for the selective control of parasitic mites on beneficial insects and for the protection of said insects from infestation and damage caused by parasitic mites with little or no concommitant harm to the beneficial host insect are needed.

SUMMARY OF THE INVENTION

The present invention provides a method for the control of parasitic mites in the presence of beneficial insects which comprises contacting said mites, their breeding grounds or habitat with a parasiticidally effective amount of tebufenpyrad. The invention further provides a method for the protection of beneficial insects from infestation and damage caused by parasitic mites which comprises applying to said insects their breeding ground or habitat a parasiticidally effective amount of tebufenpyrad.

DETAILED DESCRIPTION OF THE INVENTION

Beneficial insects such as Apidae, for example, Apinae (honeybees), Bombinae (bumblebees) and Euglossinae (orchid bees) are susceptible to attack and infestation by parasitic mites, particularly mites such as *Varroa jacobsoni* (Varroa mites), *Acarapis woodi* (tracheal mites) and *Tropilaelaps clareae*. These parasites feed on the blood via the insect's trachea (tracheal mites) or via the cuticle from the brood or adult (Varroa mites) or the larvae (*T. clareae*) causing physical deformation, deterioration and death. Further, parasitic mites may either transmit or "trigger" viruses in honeybees and other beneficial insects. Currently, a plague of parasitic mites has caused significant global concern over the present and future populations of essential agronomically important insects such as the honeybee.

Heretofore, known methods to control insect parasites may be unpredictable, such as the use of menthol for tracheal mites, or may be compromised by resistance problems, such as the overuse of fluvalinate for Varroa mites. Surprisingly, it has now been found that N-(4-t-butylbenzyl)-4-chloro-3-ethyl-1-methylpyrazole-5-carboxamide, hereinafter designated tebufenpyrad, may be used to effectively control parasitic mites in the presence of beneficial insects and for the protection of said insects from the infestation and damage caused by parasitic mites. Tebufenpyrad and methods for the preparation thereof are described in U.S. Pat. No. 4,950,668. Advantageously, the method of the invention may be used to control both the Varroa mite and the tracheal mite in the presence of beneficial insects, particularly honeybees, with little or no significant harmful effect to the insect host.

In actual practice the tebufenpyrad may be applied to the beneficial insect breeding ground or habitat such as a beehive, nest, brood chamber, or the like using a conventional delivery system. Effective amounts of tebufenpyrad are clearly very important to the invention and will vary according to the miticidal sensitivity of the beneficial insect species, the size of the brood chamber, the degree of mite infestation, the insect population density, habitat construction, weather conditions, the timing of the beneficial insect life cycle, and the like. In the present specification including the claims, "parasiticidally effective" is defined to be less than the effective $LD_{50}$ for the beneficial insect (dosage rate required to obtain 50% mortality of healthy uninfected insects), but sufficient to control or suppress the parasitic mite infestation. In general, parasiticidally effective amounts may be about 0.001–1.0 μg per insect, preferably about 0.006–0.60μg per insect.

For a more clear understanding of the invention, the following examples are set forth below. These examples are merely illustrative and are not understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

EXAMPLE 1

Evaluation Of The Efficacy Of Test Compound Against *Varroa jacobsoni* Parasites In this evaluation, honeybees (*Apis mellifera*) taken from hives which are 70–90% infested with *Varroa jacobsoni* (Varroa mites) are chilled to immobilize the bees. A 1 μl droplet of an acetone solution of tebufenpyrad is applied to the dorsal abdomen of each bee. Control bees receive 1 μl droplet of acetone. A total of 50–52 bees are treated for each dose rate tested. Treatment dose rates are based upon the $LD_{50}$ (dose rate required to obtain 50% mortality of healthy uninfected bees) of tebufenypyrad and are set at 10% of the $LD_{50}$ and subsequent 10-fold dilution thereof. The treated bees are placed in an incubator at 31° C. in the dark and fed 50% sugar water ad libitum for 5 days. After incubation, the bees are examined for mortality and mite infestation. The results are shown in Table I below, as % mortality of the total of the bees and the total of the mites.

TABLE I

| Test Compound | Dose (μg/bee) | % Mortality Bees | % Mortality Parasites |
|---|---|---|---|
| Tebufenpyrad | 0.006 | 24 | 58 |
| Tebufenpyrad | 0.06 | 25 | 44 |
| Tebufenpyrad | 0.6 | 28 | 92 |
| Control | 0 | 14 | 0 |

EXAMPLE 2

Evaluation Of The Efficacy Of Test Compound Against *Acarapis woodi* Parasites

In this evaluation, honeybees (*Apis mellifera*) which are infested with *Acarapis woodi* (trachea mites) are dissected to remove the infested tracheae. Glass microscope slides are dipped into acetone solutions of tebufenpyrad (500 ppm)and the acetone is allowed to evaporate. Infested tracheae are placed directly on the treated slides. The mites are removed from the tracheae by dissection and forced to walk across the treated area. The elapsed time is recorded for 100% mortality, i.e. no movement is observed upon agitation. The results are shown in Table II below.

TABLE II

|  | Rep. 1 | | Rep. 2 | | Rep. 3 | |
| --- | --- | --- | --- | --- | --- | --- |
| Test Compound | No. mites | Time[1] | No. mites | Time[1] | No. Mites | Time[1] |
| Tebufenpyrad | 7 | 8.5 | 10 | 8 | 7 | 8 |
| Control | 6 | >35 | 4 | >25 | — | — |

[1]Time required in minutes to achieve 100% mortality.

EXAMPLE 3

Field Evaluation Of The Efficacy Of Test Compound Against *Varroa jacobsoni* Parasites In this evaluation, two *Varroa jacobsoni* infested beehives are monitored for the extent of infestation using stickyboards inserted at the bottom of the hive. Data are presented as the number of mites trapped on the stickyboard per day. Two strips (2.5×17 cm) containing 18% tebufenpyrad dissolved in a 60:40 beeswax:lard (Crisco®) mixture are inserted into each hive brood chamber as per standard practice. One day after treatment, the stickyboards are removed and the dead mites counted. The results are shown on Table III below.

TABLE III

| Compound | Hive | Pretreatment mites/day | Treatment[1] mites/day |
| --- | --- | --- | --- |
| Tebufenpyrad | 1 | 101 | 1777 |
| Tebufenpyrad | 2 | 66 | 1080 |

[1]Count taken 24 hours after treatment

What is claimed is:

1. A method for the protection of beneficial insects from damage caused by parasitic mites selected from the group consisting of *Varroa jacobsoni, Acarapis woodi* and *Tropilaelaps clareae* which comprises applying to said insects, their brood chamber or habitat a parasiticidally effective amount of tebufenpyrad.

2. The method according to claim 1 wherein the beneficial insects are Apidae.

3. The method according to claim 2 wherein the Apidae are Apinae, Euglossinae or Bombinae.

4. The method according to claim 3 wherein the Apidae are Apinae and the Apinae are *Apis mellifera*.

5. The method according to claim 4 wherein the parasitic mites are *Varroa jacobsoni* or *Acarapis woodi*.

6. A method for the control of parasitic mites selected from the group consisting of *Varroa jacobsoni, Acarapis woodi* and *Tropilaelaps clareae* in the presence of beneficial insects which comprises contacting said mites, their brood chamber or habitat with a parasiticidally effective amount of tebufenpyrad.

7. The method according to claim 6 wherein the beneficial insects are Apidae.

8. The method according to claim 7 wherein the Apidae are Apinae, Euglossinae or Bombinae.

9. The method according to claim 8 wherein the Apidae are Apinae and the Apinae are *Apis mellifera*.

10. The method according to claim 9 wherein the parasitic mites are *Varroa jacobsoni* or *Acarapis woodi*.

11. The method according to claim 10 wherein the parasiticidally effective amount is about 0.001–1.0 µg per insect.

12. The method according to claim 11 wherein the parasiticidally effective amount is about 0.006–0.6 µg per insect.

13. The method according to claim 1 wherein the parasiticidally effective amount is about 0.001–1.0 µg per insect.

14. The method according to claim 13 wherein the parasiticidally effective amount is about 0.006–0.6 µg per insect.

15. The method according to claim 1 wherein the mites are *Varroa jacobsoni*.

16. The method according to claim 1 wherein the mites are *Acarapis woodi*.

17. The method according to claim 1 wherein the mites are *Tropilaelaps clareae*.

* * * * *